US012673126B2

(12) United States Patent
Zhu et al.

(10) Patent No.: US 12,673,126 B2
(45) Date of Patent: Jul. 7, 2026

(54) HIGH TEMPERATURE STERILIZABLE ADHESIVE ARTICLES

(71) Applicant: Solventum Intellectual Properties Company, Maplewood, MN (US)

(72) Inventors: Dong-Wei Zhu, North Oaks, MN (US); Jennifer S. Bangle, Cottage Grove, MN (US); Douglas J. Betts, Mendota Heights, MN (US)

(73) Assignee: Solventum Intellectual Properties Company, Eagan, MN (US)

( * ) Notice: Subject to any disclaimer, the term of this patent is extended or adjusted under 35 U.S.C. 154(b) by 1144 days.

(21) Appl. No.: 17/639,789

(22) PCT Filed: Aug. 20, 2020

(86) PCT No.: PCT/IB2020/057834
§ 371 (c)(1),
(2) Date: Mar. 2, 2022

(87) PCT Pub. No.: WO2021/053430
PCT Pub. Date: Mar. 25, 2021

(65) Prior Publication Data
US 2022/0323628 A1      Oct. 13, 2022

Related U.S. Application Data

(60) Provisional application No. 62/903,048, filed on Sep. 20, 2019.

(51) Int. Cl.
| | |
|---|---|
| *C09J 133/08* | (2006.01) |
| *A61L 2/07* | (2006.01) |
| *A61L 2/28* | (2006.01) |
| *A61L 103/15* | (2026.01) |
| *C08K 5/5435* | (2006.01) |

(52) U.S. Cl.
CPC .................................... *A61L 2/28* (2013.01); *A61L 2/07* (2013.01); *C09J 133/08* (2013.01); *A61L 2103/15* (2026.01); *C08K 5/5435* (2013.01); *Y10T 428/2891* (2015.01)

(58) Field of Classification Search
None
See application file for complete search history.

(56) References Cited

U.S. PATENT DOCUMENTS

| | | | |
|---|---|---|---|
| 3,311,084 A | 3/1967 | Edenbaum et al. |
| 3,523,011 A | 8/1970 | Bhiwandker et al. |
| 4,448,548 A | 5/1984 | Foley et al. |
| 4,737,559 A | 4/1988 | Kellen et al. |
| 5,506,279 A | 4/1996 | Babu et al. |
| 5,518,763 A | 5/1996 | Patnode et al. |
| 5,780,098 A | 7/1998 | Battles et al. |
| 5,922,428 A | 7/1999 | Pufahl et al. |
| 5,968,479 A | 10/1999 | Ito et al. |
| 6,083,856 A | 7/2000 | Joseph et al. |
| 6,238,623 B1 | 5/2001 | Amhof et al. |
| 7,744,997 B2 | 6/2010 | Birkholz et al. |
| 8,197,775 B2 | 6/2012 | Johnston et al. |
| 8,338,128 B2 | 12/2012 | Lye et al. |
| 8,343,437 B2 | 1/2013 | Patel et al. |
| 9,086,489 B2 | 7/2015 | Patel et al. |
| 9,146,246 B2 | 9/2015 | Battrell et al. |
| 9,170,245 B2 | 10/2015 | Landgrebe et al. |
| 9,176,103 B2 | 11/2015 | Whitman et al. |
| 9,839,712 B2 | 12/2017 | Bommarito et al. |
| 2006/0182655 A1 | 8/2006 | Zou et al. |
| 2010/0068820 A1 | 3/2010 | Meathrel et al. |
| 2012/0108734 A1* | 5/2012 | Ogawa ..................... C09J 7/385 |
| | | | 524/558 |
| 2014/0079589 A1 | 3/2014 | Landgrebe et al. |
| 2016/0022853 A1 | 1/2016 | Hajime et al. |
| 2016/0349224 A1 | 12/2016 | Patel et al. |
| 2017/0307573 A1 | 10/2017 | Bala et al. |
| 2018/0024011 A1 | 1/2018 | Patel et al. |

FOREIGN PATENT DOCUMENTS

| | | | | |
|---|---|---|---|---|
| CN | 103764781 | | 4/2014 | |
| EP | 0022284 A1 | | 1/1981 | |
| EP | 0105420 A1 * | | 4/1984 | ........... G01N 31/226 |
| EP | 2762544 A1 | | 8/2014 | |
| FR | 1461252 A | | 12/1966 | |
| JP | 61007369 A | | 1/1986 | |
| JP | 2005046367 A | | 2/2005 | |
| JP | 2017123976 A | | 7/2017 | |
| WO | 2014151336 A1 | | 9/2014 | |
| WO | 2017112562 A1 | | 9/2014 | |
| WO | 2017121871 A1 | | 7/2017 | |

OTHER PUBLICATIONS

International Search report for PCT International Application No. PCT/IB2020/057834 mailed on Jan. 15, 2021, 7 pages.

* cited by examiner

*Primary Examiner* — Anish P Desai

(57) ABSTRACT

Sterilization indicators include a first substrate and a second substrate. The first substrate has a compartment containing a fusible indicator material, and a channel in contact with the compartment for the molten indicator material to flow, and a wicking material in contact with the channel. The second substrate has a transparent segment aligned to overlay the wicking material. A high temperature sealing pressure sensitive adhesive layer adheres the first substrate to the second substrate. The adhesive layer includes a (meth)acrylate-based pressure sensitive adhesive matrix and a high temperature sealing agent. The high temperature sealing agent is essentially unreactive at ambient temperature but upon exposure to elevated temperatures forms a heat-sealed adhesive bond.

14 Claims, 1 Drawing Sheet

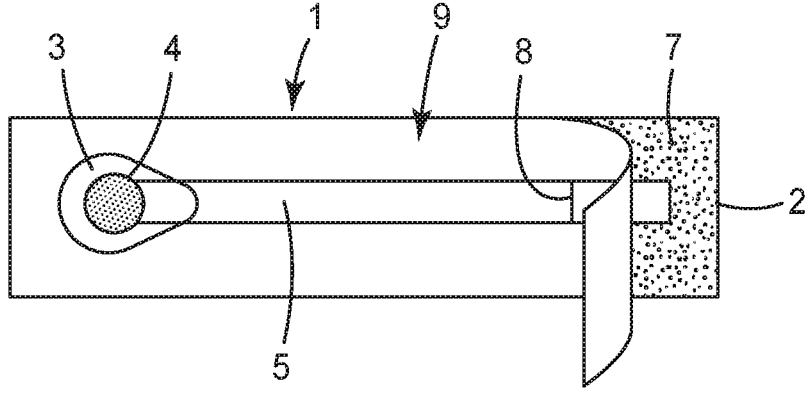

HIGH TEMPERATURE STERILIZABLE ADHESIVE ARTICLES

FIELD OF THE DISCLOSURE

This disclosure relates to pressure sensitive adhesive articles that increase adhesion upon exposure to elevated temperatures.

BACKGROUND

Hospital utensils, such as surgical instruments, undergo sterilization for each use. Steam Sterilization is a simple yet very effective decontamination method. Steam Sterilization is achieved by exposing products to saturated steam at high temperatures, typically 121° C.-135° C. (250° F.-275° F.), although a variety of temperatures are used. Products are placed in a device called an autoclave and heated through pressurized steam to kill all microorganisms including spores. The device's exposure time to steam can vary, typically it is between 3 to 30 minutes.

It is important to gauge the sterilization process so that the user may be assured that the utensils have, in fact, been subjected to the well-defined conditions necessary to render the material free of living organisms with a high probability of success. A variety of techniques and devices have been developed to determine if the well-defined conditions have been achieved.

SUMMARY

This disclosure relates to pressure sensitive adhesive articles that increase adhesion upon exposure to elevated temperatures. A wide range of articles are disclosed, especially sterilization indicators, as well as methods of using these articles.

Disclosed herein are articles comprising a first substrate with a first major surface and a second major surface, a second substrate with a first major surface and a second major surface, and a high temperature sealing pressure sensitive adhesive layer in contact with at least a portion of the second major surface of the first substrate and the first major surface of the second substrate. The pressure sensitive adhesive layer comprises a (meth)acrylate-based pressure sensitive adhesive matrix and a high temperature sealing agent. The high temperature sealing agent is essentially unreactive with the (meth)acrylate-based pressure sensitive adhesive matrix at ambient temperature and reacts with the (meth)acrylate-based pressure sensitive adhesive matrix at temperatures of at least 100° C. to form a heat-sealed adhesive bond, where the heat-sealed adhesive bond has increased adhesion compared to the bond of the pressure sensitive adhesive layer without the high temperature sealing agent.

In some embodiments, the articles are sterilization indicators. The sterilization indicators comprise a first substrate and a second substrate. The first substrate has a first major surface and a second major surface, where the second major surface comprises a compartment containing a fusible indicator material, and a channel in contact with the compartment for the molten indicator material to flow, and a wicking material in contact with the channel. The second substrate has a first major surface and a second major surface, where the second major surface comprises a transparent segment aligned to overlay the wicking material. A high temperature sealing pressure sensitive adhesive layer is in contact with at least a portion of the second major surface of the first substrate and the first major surface of the second substrate. The pressure sensitive adhesive layer comprises a (meth) acrylate-based pressure sensitive adhesive matrix and a high temperature sealing agent. The high temperature sealing agent is essentially unreactive with the (meth)acrylate-based pressure sensitive adhesive matrix at ambient temperature and reacts with the (meth)acrylate-based pressure sensitive adhesive matrix at temperatures of at least 100° C. to form a heat-sealed adhesive bond. The heat-sealed adhesive bond has increased adhesion compared to the bond of the pressure sensitive adhesive layer without the high temperature sealing agent.

Also disclosed herein are methods of using a sterilization indicator comprising providing a sealable sterilization package, providing medical instruments to be sterilized, providing a sterilization indicator, sealing the medical instruments and sterilization indicator in the sterilization package, and heating the sealed package to sterilize the medical instruments. The sterilization indicator comprises a first substrate and a second substrate. The first substrate has a first major surface and a second major surface, where the second major surface comprises a compartment containing a fusible indicator material, and a channel in contact with the compartment for the molten indicator material to flow, and a wicking material in contact with the channel. The second substrate has a first major surface and a second major surface, where the second major surface comprises a transparent segment aligned to overlay the wicking material. A high temperature sealing pressure sensitive adhesive layer is in contact with at least a portion of the second major surface of the first substrate and the first major surface of the second substrate. The pressure sensitive adhesive layer comprises a (meth) acrylate-based pressure sensitive adhesive matrix and a high temperature sealing agent. The high temperature sealing agent is essentially unreactive with the (meth)acrylate-based pressure sensitive adhesive matrix at ambient temperature and reacts with the (meth)acrylate-based pressure sensitive adhesive matrix at temperatures of at least 100° C. to form a heat-sealed adhesive bond. The heat-sealed adhesive bond has increased adhesion compared to the bond of the pressure sensitive adhesive layer without the high temperature sealing agent.

BRIEF DESCRIPTION OF THE DRAWINGS

The present application may be more completely understood in consideration of the following detailed description of various embodiments of the disclosure in connection with the accompanying drawings.

FIG. 1 is a top sectional view of an embodiment of a sterilization indicator of the present disclosure, with a portion of the top substrate peeled back.

In the following description of the illustrated embodiments, reference is made to the accompanying drawings, in which is shown by way of illustration, various embodiments in which the disclosure may be practiced. It is to be understood that the embodiments may be utilized and structural changes may be made without departing from the scope of the present disclosure. The FIGURES are not necessarily to scale. Like numbers used in the FIGURES refer to like components. However, it will be understood that the use of a number to refer to a component in a given FIGURE is not intended to limit the component in another FIGURE labeled with the same number.

DETAILED DESCRIPTION

Hospital utensils, such as surgical instruments, undergo sterilization for each use. Steam Sterilization is a simple yet very effective decontamination method. Steam Sterilization is achieved by exposing products to saturated steam at high temperatures, typically 121° C.-135° C. (250° F.-275° F.), although a variety of temperatures are used. Products are placed in a device called an autoclave and heated through pressurized steam to kill all microorganisms including spores. The device's exposure time to steam can vary, typically it is between 3 to 30 minutes.

It is important to gauge the sterilization process so that the user may be assured that the utensils have, in fact, been subjected to the well-defined conditions necessary to render the material free of living organisms with a high probability of success. A variety of techniques and devices have been developed to determine if the well-defined conditions have been achieved.

Among the techniques and devices that have been developed are sterilization indicators. The indicators are placed in the autoclave along with the instruments to be sterilized. The sterilization indicator includes a mechanism that indicates the temperature and temperature duration achieved during the sterilization process.

U.S. Pat. No. 4,448,548 (Foley), describes a steam sterilization indicator that includes an encapsulated fusible material in an embossment of the indicator. The fusible material is in tablet form, such that upon melting the fusible material is absorbed by a wicking material in a wicking strip to produce a color front that provides an indication of the time and temperature in the presence of steam.

Steam sterilization indicators such as those described by Foley are very useful for a wide range of reasons. They are simple and inexpensive to create thus permitting them to be used widely, they are simple to use, as they merely are placed in the autoclave along with the instruments to be sterilized, and they provide a clear indication that sterilization conditions have been achieved.

These steam sterilization indicators also have shortcomings. In general, the indicators have a thin aluminum backing with an embossment to hold a fusible material in tablet form, a wicking strip in close proximity to the fusible material tablet, and a clear plastic layer covering the tablet and wicking strip and adhered to the aluminum backing. Generally, the clear plastic layer covering is adhered to the aluminum backing by a pressure sensitive adhesive. Pressure sensitive adhesive compositions are well known to those of ordinary skill in the art to possess properties including the following: (1) aggressive and permanent tack, (2) adherence with no more than finger pressure, (3) sufficient ability to hold onto an adherend, and (4) sufficient cohesive strength to be cleanly removable from the adherend. Materials that have been found to function well as pressure sensitive adhesives are polymers designed and formulated to exhibit the requisite viscoelastic properties resulting in a desired balance of tack, peel adhesion, and shear holding power. Obtaining the proper balance of properties is not a simple process. Pressure sensitive adhesives are viscoelastic materials, meaning they simultaneously have elastic properties (such as the properties of rubber materials) and viscous flow properties (such as the property of honey). Thus, as the temperature rises, the viscous flow component of pressure sensitive adhesives can become more pronounced and the adhesive loses cohesive strength and can even begin to flow. Therefore, steam sterilization indicators that have substrates adhesively bonded with pressure sensitive adhesives can have the adhesive bonds fail by delamination under the high heat and humidity conditions of steam sterilization.

In moving-front steam chemical indicators, the ink migrates along the paper substrate as it is exposed to increased time and temperature in a steam sterilization process. The reactive ink is intended to remain contained within the laminated layers of the integrator under normal use conditions. Leaker defects can occur in a variety of ways, besides total delamination as described above. In some cases, the ink migration path deviates away from the center of the integrator at the wicking strip towards the outer edges of the device, resulting in stress applied to the device during the steam sterilization process. When the ink migration reaches the top or bottom edge of the integrator, a leaker defect may occur as the ink now has a path out of the integrator.

One possible technique for overcoming the propensity of pressure sensitive adhesives to weaken upon exposure to heat under conditions of steam sterilization is to increase the cohesive strength of the pressure sensitive adhesive by crosslinking. However, in order to retain the desirable pressure sensitive adhesive properties, there are tradeoffs with this approach, since the crosslinking of pressure sensitive adhesives adversely affects the tackiness of the pressure sensitive adhesive. Thus, there is a limit to the amount of crosslinking that can be carried out within a pressure sensitive adhesive without adversely affecting the adhesive properties.

In this disclosure, pressure sensitive adhesive layers are disclosed that are (meth)acrylate pressure sensitive adhesives that include high temperature sealing agents. The high temperature sealing agent is essentially unreactive at ambient temperatures but upon exposure to elevated temperatures forms a heat-sealed layer where the heat-sealed layer has a higher adhesion than the pressure sensitive adhesive without the high temperature sealing agent. In this way, the pressure sensitive adhesive functions as a pressure sensitive adhesive layer at room temperature permitting the assembly of articles such as sterilization indicators. However, upon the application of heat to the pressure sensitive adhesive layer, such as by steam sterilization, the layer forms a heat-sealed bond. The formation of the heat-sealed bond increases the adhesion of the adhesive bond and prevents viscous flow of the viscoelastic pressure sensitive adhesive.

Disclosed herein are articles that include two substrates and the heat-sealable pressure sensitive adhesive layers. In some embodiments, the articles are sterilization indicators.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. For example, reference to "a layer" encompasses embodiments having one, two or more layers. As used in this specification and the appended claims, the term "or" is generally employed in its sense including "and/or" unless the content clearly dictates otherwise.

The term "adhesive" as used herein refers to polymeric compositions useful to adhere together two adherends. Examples of adhesives are pressure sensitive adhesives.

Pressure sensitive adhesive compositions are well known to those of ordinary skill in the art to possess properties including the following: (1) aggressive and permanent tack, (2) adherence with no more than finger pressure, (3) sufficient ability to hold onto an adherend, and (4) sufficient cohesive strength to be cleanly removable from the adherend. Materials that have been found to function well as pressure sensitive adhesives are polymers designed and formulated to exhibit the requisite viscoelastic properties resulting in a desired balance of tack, peel adhesion, and shear holding power. Obtaining the proper balance of properties is not a simple process.

The term "(meth)acrylate" refers to monomeric acrylic or methacrylic esters of alcohols. Acrylate and methacrylate monomers or oligomers are referred to collectively herein as "(meth)acrylates". Materials referred to as "(meth)acrylate functional" are materials that contain one or more (meth) acrylate groups.

As used herein the term "polymer" refers to a macromolecule that is a homopolymer or a copolymer. As used herein, the term "homopolymer" refers to a polymeric material that is the reaction product of one monomer, and the term "copolymer" refers to a polymeric material that is the reaction product of at least two different monomers.

The term "essentially unreactive at ambient temperature" as used herein when referring to pressure sensitive adhesive layers with high temperature sealing agents, indicates that the high temperature sealing agents do not appreciably react with the pressure sensitive adhesive at ambient temperature. It is well understood in the chemical arts that thermally activated compounds, such as are present in the high temperature sealing agents, may have low activity at ambient temperature, however they are designed to remain largely unreactive until elevated temperatures are applied to them.

The term "alkyl" refers to a monovalent group that is a radical of an alkane, which is a saturated hydrocarbon. The alkyl can be linear, branched, cyclic, or combinations thereof and typically has 1 to 20 carbon atoms. In some embodiments, the alkyl group contains 1 to 18, 1 to 12, 1 to 10, 1 to 8, 1 to 6, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl. Simple alkyl groups are abbreviated herein as methyl=Me, ethyl=Et, n-propyl=Pr.

The term "aryl" refers to a monovalent group that is aromatic and carbocyclic. The aryl can have one to five rings that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl. The simple aryl group phenyl is abbreviated herein as Ph.

The term "alkoxy" refers to a monovalent group of formula —OR' where IV is an alkyl group.

The terms "room temperature" and "ambient temperature" are used interchangeably to mean temperatures in the range of 20° C. to 25° C.

The terms "Tg" and "glass transition temperature" are used interchangeably. If measured, Tg values are determined by Differential Scanning calorimetry (DSC) at a scan rate of 10° C./minute, unless otherwise indicated. Typically, Tg values for copolymers are not measured but are calculated using the well-known Fox Equation, using the monomer Tg values provided by the monomer supplier, as is understood by one of skill in the art.

A wide range of heat-sealable articles are disclosed herein. One particularly suitable class of heat-sealable articles is the sterilization indicators described in greater detail below. Typically, the heat-sealable articles comprise a first substrate with a first major surface and a second major surface, a second substrate with a first major surface and a second major surface, and a high temperature sealing pressure sensitive adhesive layer in contact with at least a portion of the second major surface of the first substrate and the first major surface of the second substrate. The pressure sensitive adhesive layer comprises a (meth)acrylate-based pressure sensitive adhesive matrix and a high temperature sealing agent, wherein the high temperature sealing agent is essentially unreactive with the (meth)acrylate-based pressure sensitive adhesive matrix at ambient temperature and reacts with the (meth)acrylate-based pressure sensitive adhesive matrix at temperatures of at least 100° C. to form a heat-sealed adhesive bond, wherein the heat-sealed adhesive bond has increased adhesion compared to the bond of the pressure sensitive adhesive layer without the high temperature sealing agent.

The pressure sensitive adhesive layer includes a (meth) acrylate-based pressure sensitive adhesive matrix and a high temperature sealing agent. A wide range of (meth)acrylate-based pressure sensitive adhesive matrices are suitable for use in the pressure sensitive adhesive layers of the present disclosure. Particularly suitable (meth)acrylate-based pressure sensitive adhesives include copolymers derived from: (A) at least one monoethylenically unsaturated alkyl (meth) acrylate monomer (i.e., alkyl acrylate and alkyl methacrylate monomer); and (B) at least one monoethylenically unsaturated free-radically copolymerizable acid-functional monomer. The acid-functional monomer has a homopolymer glass transition temperature (Tg) higher than that of the alkyl (meth)acrylate monomer and is one that increases the glass transition temperature and cohesive strength of the resultant copolymer. Herein, "copolymer" refers to polymers containing two or more different monomers, including terpolymers, tetrapolymers, etc.

Monomer A, which is a monoethylenically unsaturated alkyl acrylate or methacrylate (i.e., (meth)acrylic acid ester), contributes to the flexibility and tack of the copolymer. Generally, monomer A has a homopolymer Tg of no greater than about 0° C. Typically, the alkyl group of the (meth) acrylate has an average of about 1 to about 12 carbon atoms, or an average of about 4 to about 12 carbon atoms. The alkyl group can optionally contain oxygen atoms in the chain thereby forming ethers or alkoxy ethers, for example. Examples of monomer A include, but are not limited to, 2-methylbutyl acrylate, isooctyl acrylate, lauryl acrylate, 4-methyl-2-pentyl acrylate, isoamyl acrylate, sec-butyl acrylate, n-butyl acrylate, n-hexyl acrylate, 2-ethylhexyl acrylate, n-octyl acrylate, n-decyl acrylate, isodecyl acrylate, isodecyl methacrylate, and isononyl acrylate. Other examples include, but are not limited to, poly-ethoxylated or -propoxylated methoxy (meth)acrylates such as acrylates of CARBOWAX (commercially available from Union Carbide) and NK ester AM90G (commercially available from Shin Nakamura Chemical, Ltd., Japan). Suitable monoethylenically unsaturated (meth)acrylates that can be used as monomer A include isooctyl acrylate, 2-ethyl-hexyl acrylate, and n-butyl acrylate. Combinations of various monomers categorized as an A monomer can be used to make the copolymer.

Monomer B, which is a monoethylenically unsaturated free-radically copolymerizable acid-functional monomer, increases the glass transition temperature and cohesive strength of the copolymer. Generally, monomer B has a homopolymer Tg of at least about 10° C. Examples of monomer B include, but are not limited to, acrylic acid, a methacrylic acid, itaconic acid, crotonic acid, maleic acid, or fumaric acid. A particularly suitable copolymerizable acid-functional monomer is acrylic acid.

Generally, the (meth)acrylate copolymer is formulated to have a resultant Tg of less than about 0° C. and more typically, less than about −10° C. Such (meth)acrylate copolymers generally include about 60 parts to about 98 parts per hundred of at least one monomer A and about 2 parts to about 40 parts per hundred of at least one monomer B. In some embodiments, the (meth)acrylate copolymers have about 85 parts to about 98 parts per hundred or at least one monomer A and about 2 parts to about 15 parts of at least one monomer B.

As mentioned above, in some embodiments it may be desirable that the at least one (meth)acrylate copolymer further comprises a crosslinker. This crosslinking refers to the pressure sensitive adhesive matrix and is separate from the heat sealing that is affected by the high temperature sealing agent. In these crosslinked pressure sensitive adhesive matrices, typically the copolymers are prepared by the addition of crosslinking agent in addition to monomer A and monomer B as described above. A crosslinking agent is used to build the molecular weight and the strength of the (meth)acrylate copolymer. Generally, the crosslinking agent is one that is copolymerized with monomers A and B. Suitable crosslinking agents are disclosed in U.S. Pat. No. 4,737,559 (Kellen), 5,506,279 (Babu et al.), and 6,083,856 (Joseph et al.).

The crosslinking agent is used in an effective amount, by which is meant an amount that is sufficient to cause crosslinking of the pressure sensitive adhesive to provide adequate cohesive strength to produce the desired final adhesion properties to the substrate of interest. Generally, the crosslinking agent is used in an amount of about 0.1 part to about 10 parts, based on the total amount of monomers.

Another useful class of crosslinking agents contain functionality which is reactive with carboxylic acid groups on the acrylic copolymer when a carboxylic acid group is present. Examples of such crosslinkers include multifunctional aziridine, isocyanate, epoxy, and carbodiimide compounds. Examples of aziridine-type crosslinkers include, for example 1,4-bis(ethyleneiminocarbonylamino)benzene, 4,4'-bis(ethyleneiminocarbonylamino)diphenylmethane, 1,8-bis(ethyleneiminocarbonylamino)octane, and 1,1'-(1,3-phenylene dicarbonyl)-bis-(2-methylaziridine). Common polyfunctional isocyanate crosslinkers include, for example, trimethylolpropane toluene diisocyanate, tolylene diisocyanate, and hexamethylene diisocyanate.

The pressure sensitive adhesive layer also comprises a high temperature sealing agent. The high temperature sealing agent is an agent that is essentially unreactive with the (meth)acrylate pressure sensitive adhesive matrix at ambient temperatures, but upon heating to elevated temperatures, the sealing agent reacts with the (meth)acrylate pressure sensitive adhesive matrix to form a heat-sealed layer. The heat-sealed layer has higher adhesion than the pressure sensitive adhesive matrix that has not been heat-sealed.

The term high temperature sealing agent refers to agents that become activated at a temperature of at least 100° C. In some embodiments, the activation temperature may be lower such as at least 60° C., or at least 80° C., generally if the articles are exposed to these lower temperatures for longer times. In other embodiments, the activation temperature may be higher than 100° C., such as at least 121° C. It is well understood in the chemical arts that thermally activated compounds, such as are present in the high temperature sealing agents, may have low activity at ambient temperature, however they are designed to remain largely unreactive until elevated temperatures are applied to them.

Typically, the high temperature sealing agent comprises a combination of a thermal free radical generator capable of hydrogen abstraction and an acid-reactive compound. While not wishing to be bound by theory, it is believed that the use of the combination provides superior heat-sealing properties than either a thermal free radical generator capable of hydrogen abstraction or an acid-reactive compound used alone.

A wide range of thermal free radical generators capable of hydrogen abstraction are suitable. Typically, the thermal free radical generators include materials that are available as thermal free radical initiators. While not wishing to be bound by theory, it is believed that the free radical generators, upon activation forms free radicals and that these free radicals are able to extract hydrogen atoms from the (meth)acrylate copolymeric matrix to generate free radicals on the (meth)acrylate copolymeric matrix. The free radicals generated on the (meth)acrylate copolymeric matrix can form additional crosslinks between copolymers in the matrix.

A particularly suitable class of thermal free radical generators capable of hydrogen abstraction are organic peroxides such as alkyl and aryl peroxides. In some embodiments, it is desirable that the organic peroxide is activated at elevated temperatures, such as benzoyl peroxide. Other initiators include tert-butyl peroxide, tert-butyl hydroperoxide, tert-butyl peroxybenzoate, tert-butyl peroxy-2-ethylhexanoate or perketals such as 1,1-di(tert-butylperoxy)cyclohexane, commercially available from PERGAN, The Peroxide Company. If a lower activation temperature is desired such as 60° C. or 80° C., more active initiators such as the di-(4-tert.-butylcyclohexyl)-peroxydicarbonate and Methylisobutylketoneperoxide initiators commercially available from PERGAN, The Peroxide Company, can be used. In some embodiments, benzoyl peroxide is a particularly suitable thermal free radical generator.

A wide range of acid-reactive compounds are suitable for use in the high temperature sealing agents of this disclosure. Particularly suitable acid-reactive compounds are epoxy-functional compounds and multi-functional compounds comprising epoxy-functionality. In some embodiments, the acid-reactive compound is an epoxy-functional silane. Epoxy-functional silanes are often referred to as coupling agents as they have one type of functionality at one terminus (epoxy) and a different functionality at the other terminus (silane) and are used to couple different types of polymers and materials. A number of epoxy-functional silanes are suitable such as (3-glycidyloxypropyl)trimethoxysilane, (3-glycidyloxypropyl)methyldiethoxysilane, 2-(3,4-epoxy-cyclohexyl)ethyltriethoxysilane, and 2-(3,4-epoxycyclo-hexyl)ethyltrimethoxysilane commercially available from Gelest. In some embodiments, (3-glycidyloxypropyl) trimethoxysilane is particularly suitable.

In the articles of this disclosure, a wide range of substrates are suitable as the first and second substrates. The first and second substrates can be the same or different. The substrate may be a rigid substrate or a non-rigid substrate. Examples of rigid substrates include glass plates, relatively thick polymeric plates such as polymethyl methacrylate (PMMA) plates and polycarbonate (PC) plates, and the exterior surface of a device.

Examples of suitable non-rigid substrates include polymeric films and metal foils. Examples of suitable metal foils include aluminum foil, copper foil, nickel foil, brass foil, and stainless steel foil. Examples of polymeric films include films comprising one or more polymers such as cellulose acetate butyrate; cellulose acetate propionate; cellulose triacetate; poly(meth)acrylates such as polymethyl methacrylate; polyesters such as polyethylene terephthalate, and polyethylene naphthalate; copolymers or blends based on naphthalene dicarboxylic acids; polyether sulfones; polyurethanes; polycarbonates; polyvinyl chloride; syndiotactic polystyrene; cyclic olefin copolymers; and polyolefins including polyethylene and polypropylene such as cast and biaxially oriented polypropylene. The substrate may comprise single or multiple layers, such as polyethylene-coated polyethylene terephthalate. The substrate may be primed or treated to impart some desired property to one or more of its surfaces. Examples of such treatments include corona, flame, plasma and chemical treatments.

One specific type of article disclosed herein are sterilization indicators. In some embodiments, the sterilization indicators comprise a first substrate with a first major surface and a second major surface, where the second major surface comprises a compartment. The compartment is an embossment or depression in the second major surface of the first substrate, and a channel in contact with the compartment. The compartment contains a fusible indicator material, and the channel in contact with the compartment contains a wicking material into which the molten indicator material can flow. The indicator further comprises a second substrate with a first major surface and a second major surface, where the second major surface comprises a transparent segment aligned to overlay the wicking material. The indicator further comprises a high temperature sealing pressure sensitive adhesive layer in contact with at least a portion of the second major surface of the first substrate and the first major surface of the second substrate. The pressure sensitive adhesive layer comprises a (meth)acrylate-based pressure sensitive adhesive matrix and a high temperature sealing agent, where the high temperature sealing agent is essentially unreactive with the (meth)acrylate-based pressure sensitive adhesive matrix at ambient temperature and reacts with the (meth) acrylate-based pressure sensitive adhesive matrix at temperatures of at least 100° C. to form a heat-sealed adhesive bond. The heat-sealed adhesive bond has increased adhesion compared to the bond of the pressure sensitive adhesive layer that has not been heat-sealed, that is to say a pressure sensitive adhesive layer that does not contain the high temperature sealing agent.

Depending upon the high temperature sealing agent used, the heat-sealing pressure sensitive adhesive can be activated to heat-seal at a range of different temperatures. In some embodiments, the heat-sealing pressure sensitive adhesive can be activated to heat-seal at 60° C., at 80° C., at 100° C., or even at 121° C. In some embodiments, 121° C. (250° F.) is particularly suitable as this is a temperature commonly used for steam sterilization. A wide variety of sterilization criteria have been developed, such as for example, the ISO 11140-1 (2014) standard.

Indicators of this disclosure may be more fully understood from the FIGURE. FIG. 1 is a top view of indicator 1. Indicator 1 has first substrate 2, typically a metal layer, and second substrate 9, typically a polymeric film layer. In FIG. 1, part of second substrate 9 has been peeled away from first substrate 2. First substrate 2 has embossment or depression 3 that contains fusible material tablet 4 and wicking strip 5. Position 8 along wicking strip 5 indicates when proper sterilization has occurred. Heat-sealable pressure sensitive adhesive 7, is the heat-sealable adhesive layer described in this disclosure.

The sterilization indicator comprises a pressure sensitive adhesive layer 7 that comprises a (meth)acrylate-based pressure sensitive adhesive matrix and a high temperature sealing agent. The (meth)acrylate-based pressure sensitive adhesive matrix comprises at least one (meth)acrylate copolymer comprising at least one alkyl (meth)acrylate comprising 1-12 carbon atoms, and at least one copolymerizable acid-functional monomer. The (meth)acrylate copolymer may further comprise a crosslinker. These (meth)acrylate copolymers are described in detail above.

The pressure sensitive adhesive layer of the sterilization indicators of this disclosure comprises a high temperature sealing agent that is a combination of a thermal free radical generator capable of hydrogen abstraction and an acid-reactive compound. Typically, the thermal free radical generator comprises a peroxide with an activation temperature of at least 100° C. These thermal free radical generators are described in detail above.

The high temperature sealing agent also comprises an acid-reactive compound. Typically, the acid-reactive compound comprises an epoxy-functional compound or a multifunctional compound comprising epoxy-functionality. In some embodiments, the acid-reactive compound comprises an epoxy-functional silane.

The sterilization indicators of the current disclosure include a first substrate 2 and a second substrate 9. While a wide range of substrates are suitable, in some embodiments, the first substrate 2 comprises a metal foil, and the second substrate 9 comprises a polymeric film.

A wide range of metal foils are suitable for use as the first substrate 2. The metal foil substrate provides a moisture barrier and is sufficiently malleable and flexible to permit the formation of the embossment or depression 3 and the adjacent channel suitable for containing wicking strip 5. The metal foil is of any suitable thickness that permits moisture transmission and also is able to permit the formation of the embossment or depression 3 and the adjacent channel suitable for containing wicking strip 5. Aluminum foils are particularly suitable for first substrate 2.

A wide range of polymeric films are suitable for use as second substrate 9. Second substrate 9 may comprise a single polymeric film, a multi-layer polymeric film, or a composite film. As used herein, composite film refers to a film that is not single polymeric film but has regions that are one type of polymeric film and other regions that are another type of polymeric film. In the current articles, the region of the polymeric film that overlays the embossment or depression 3 and the adjacent channel suitable for containing wicking strip 5 is optically transparent to allow visual monitoring of the indicator.

Typically, for ease of assembly, a single polymeric film is used as second substrate 9. The single polymeric film is thus generally optically transparent, permitting the embossment or depression 3 and the adjacent channel suitable for containing wicking strip 5 to be viewed. In some embodiments, the optically transparent film has a luminous transmission of at least 80% over at least a portion of the visible light spectrum (about 380-740 nanometers).

A wide range of polymeric films are suitable. Examples of suitable polymeric films include polyesters such as polyethylene terephthalate, and polyolefins including polyethylene and polypropylene such as unoriented polypropylene. The polymeric film can be of any suitable thickness, typically 25-100 micrometers (1-4 mils).

A wide variety of materials are suitable for fusible material tablet 4. The term "fusible material" is used herein consistently with the commonly used definition, namely a material that is able to fused or melted easily. In the current indicators, the fusible material melts at a selected temperature, is absorbed by the wicking strip 5, and flows within the wicking strip 5. In some embodiments, the tablet 4 comprises salicylamide.

Suitable tablets 4 are described in U.S. Pat. No. 4,448,548 (Foley), and typically include a binder such as PVP (polyvinylpyrrolidone) and may include other materials such as talc. In order to provide a visual indication, the tablet 4 typically includes a colorant, such as a heat stable dye.

A wide variety of materials are suitable for wicking strip 5. Typically, the wicking strip 5 comprises a porous material capable of wicking a liquid by capillary action. Wicking strip 5 is placed in contact with or nearly in contact with table 4 such that one end of wicking strip 5 is located within embossment 3. The wicking strip absorbs molten tablet 4 and carries the heat stable dye down the strip as a color front, as long as the temperature is high enough to maintain the tablet 4 material in the molten state. Position 8 is located at a position along wicking strip 5 such that when the color front reaches position 8, the indicator has been in an environment that has undergone sufficient sterilization.

Also disclosed herein are methods of using the sterilization indicators described above. In some embodiments the method comprises, providing a sealable sterilization package, providing medical instruments to be sterilized, providing a sterilization indicator; sealing the medical instruments and sterilization indicator in the sterilization package, and heating the sealed package to sterilize the medical instruments. Suitable sterilization indicators have been described in detail above with the heat sealable feature that permits the indicator to withstand the rigorous temperature, steam, and time criteria used to sterilize medical instruments. A wide variety of temperature and time criteria have been developed to ensure sterilization. In some embodiments, the sterilization indicator passes the ISO 11140-1 (2014) standard.

EXAMPLES

These examples are merely for illustrative purposes only and are not meant to be limiting on the scope of the appended claims. All parts, percentages, ratios, etc. in the examples and the rest of the specification are by weight, unless noted otherwise. Solvents and other reagents used were obtained from Sigma-Aldrich Chemical Company; Milwaukee, Wis. unless otherwise noted. The following abbreviations are used: cm=centimeters; in=inch; ft=feet; g=grams; min=minutes; mbar=millibar. The terms "weight %", "% by weight", and "wt %" are used interchangeably.

TABLE 1

| Abbreviations | |
| --- | --- |
| Abbreviation or Trade Designation | Description |
| IOA | Isooctyl acrylate |
| 2-EHA | 2-Ethylhexyl acrylate |
| MA | Methyl acrylate |
| BA | Butyl acrylate |

TABLE 1-continued

| Abbreviations | |
| --- | --- |
| Abbreviation or Trade Designation | Description |
| AA | Acrylic acid |
| SCK | Super-calendered kraft paper |
| PCK | Poly-coated kraft paper |

Test Methods

Robustness Testing

The prototypes were tested according to the sterilization cycle described below. The prototypes were placed in a Steam Sterilization Chamber. The sterilization cycle that was used involves applying multiple rapid vacuums in a conditioning phase to 125 mbar prior to steam exposure phase. The exposure phase was held at 135° C.+/−0.5° C. for 18:00 minutes+/−1 second. A rapid vacuum is then applied to 65 mbar before completing the cycle. The prototypes were examined, and the results are presented in Table 5.

In Table 5: "Foil/Film Delamination (%)" refers to the percentage of prototypes having noticeable adhesive failure between the foil and film; "Leaker (%)" refers to the percentage of prototypes that showed noticeable ink leakage from the device; and, "Ink Migration (%)" refers to the percentage of devices in which the ink remained contained but had noticeably migrated outside the wicking region into the adhesive layer.

Adhesives

Stock solutions of reagents were prepared according to Table 2. Adhesive solutions were prepared according to Table 3 by mixing the reagent solutions at ambient temperature for 30 minutes before coating.

TABLE 2

| Stock solutions of reagents used in adhesive formulations. | | |
| --- | --- | --- |
| Solution # | Type | Name (Source, location) |
| 1 | Acrylic Adhesive Solution (IOA/AA = 90/10, 41 wt % solution in ethyl acetate) | Prepared according to Ulrich, U.S. Pat. No. RE 24,906. |
| 2 | Acrylic Adhesive Solution (IOA/MA/AA = 57.5/35/7.5, 26 wt % solution in ethyl acetate) | Prepared according to Ulrich, U.S. Pat. No. RE 24,906. |
| 3 | Acrylic Adhesive Solution (2-EHA/BA/AA = 48/47.5/4.5, 35 wt % solution in ethyl acetate) | Prepared according to Ulrich, U.S. Pat. No. RE 24,906. |
| 4 | Acrylic Adhesive Solution (Tackified IOA/AA = 93/7, 33 wt % in ethyl acetate) | Prepared according to Ulrich, U.S. Pat. No. RE 24,906. |
| 5 | 1,1'-isophthaloyl-bis-1-methylaziridine (C.A.S. 7652-64-4), 5% toluene solution | Prepared according to the method described in U.S. Pat. No. 8,507,612 |
| 6 | Bis(3,4-epoxycyclohexylmethyl) adipate (20% ethyl acetate solution) | Epoxy 28 (Synasia, Metuchen, NJ) |
| 7 | Methyldiethanolamine (20% ethyl acetate solution) | Methydiethanol Amine (Available from MilliporeSigma, St. Louis, MO) |
| 8 | Benzoyl Peroxide (10% ethyl acetate solution) | Luperox A75 (Arkema, King of Prussia, PA) |
| 9 | Glycidoxypropyltrimethoxysilane (10% ethyl acetate solution) | Andisil 187 Silane (AB Specialty Silicones, Waukegan, IL) |

TABLE 3

Adhesive formulations. All amounts are grams of stock solution as specified in Table 2.

| Formulation No. | Solution number (corresponding to Table 2) | | | | | | | | |
|---|---|---|---|---|---|---|---|---|---|
| | 1 | 2 | 3 | 4 | 5 | 6 | 7 | 8 | 9 |
| L1 | 2,000 g | | | | 16.4 g | | | | |
| L2 | 2,000 g | | | | 16.4 g | 10.3 g | | | |
| L3 | 2,000 g | | | | 16.4 g | 20.6 g | | | |
| L4 | 2,000 g | | | | | 10.3 g | | | |
| L5 | 2,000 g | | | | 16.4 g | 20.6 g | 4.1 g | | |
| L6 | 2,000 g | | | | 24.6 g | | | | |
| L7 | 2,000 g | | | | 32.9 g | | | | |
| L8 | | 2,000 g | | | 10.4 g | | | | |
| L9 | | | 2,000 g | | 14.0 g | | | | |
| L10 | | | | 2,000 g | 13.2 g | | | | |
| L11 | | 2,000 g | | | 20.8 g | | | | |
| L12 | | | 2,000 g | | 28.1 g | | | | |
| L13 | | | | 2,000 g | 26.5 g | | | | |
| L14 | 1,000 g | | | | 24.7 g | | | | |
| L15 | 1,000 g | | | | 32.9 g | | | | |
| L16 | 1,000 g | | | | 41.2 g | | | | |
| L17 | 1,000 g | | | | 8.2 g | | | 6.2 g | |
| L18 | 1,000 g | | | | 8.2 g | | | 12.3 g | |
| L19 | 1,000 g | | | | 8.2 g | | | | 6.2 g |
| L20 | 1,000 g | | | | 8.2 g | | | | 12.3 g |
| L21 | 1,000 g | | | | 8.2 g | | | 4.1 g | 12.4 g |
| L22 | 1,000 g | | | | 8.2 g | | | 6.2 g | 6.2 g |
| L23 | 1,000 g | | | | 8.2 g | | | 8.2 g | 8.2 g |
| L24 | 1,000 g | | | | 8.2 g | | | 12.4 g | 4.1 g |
| L25 | 1,000 g | | | | 8.2 g | | | 10.3 g | 10.3 g |

Coating and Converting

The adhesive formulations were solvent coated onto six-inch-wide (15 cm) PCK release liner or SCK release liner with both sides silicone-coated (adhesive was coated on the "tight" side of the release liners). The liners coated with the adhesive formulations were dried in ovens ranging from 80°-180° F. (27-82° C.). The coating die gap was adjusted to match the target coating weights provided in Table 4 in grains/4 inch×6 inch (0.065 g/10 cm×15 cm). The adhesive coated rolls were then slit into 50 mm (1.969 in.) wide rolls.

TABLE 4

Coating weights of adhesive formulations as specified in Table 3.

| Coating Number | Formulation No. | Liner | Adhesive Composition | Coating Weight (grains/ 4" × 6") |
|---|---|---|---|---|
| 1 | L1 | PCK | IOA/AA = 90/10 | 16.1 |
| 2 | L2 | PCK | IOA/AA = 90/10 | 17.8 |
| 3 | L3 | PCK | IOA/AA = 90/10 | 16.0 |
| 4 | L4 | PCK | IOA/AA = 90/10 | 17.6 |
| 5 | L3 | PCK | IOA/AA = 90/10 | 8.1 |
| 6 | L5 | PCK | IOA/AA = 90/10 | 8.2 |
| 7 | L3 | PCK | IOA/AA = 90/10 | 12.0 |
| 8 | L5 | PCK | IOA/AA = 90/10 | 11.9 |
| 9 | L3 | PCK | IOA/AA = 90/10 | 10.1 |
| 10 | L6 | PCK | IOA/AA = 90/10 | 9.8 |
| 11 | L7 | PCK | IOA/AA = 90/10 | 10.0 |
| 12 | L3 | PCK | IOA/AA = 90/10 | 15.2 |
| 13 | L6 | PCK | IOA/AA = 90/10 | 15.1 |
| 14 | L7 | PCK | IOA/AA = 90/10 | 15.1 |
| 15 | L3 | PCK | IOA/AA = 90/10 | 19.9 |
| 16 | L6 | PCK | IOA/AA = 90/10 | 20.2 |
| 17 | L7 | PCK | IOA/AA = 90/10 | 20.0 |
| 18 | L8 | SCK | IOA/MA/AA = 57.5/35/7.5 | 9.8 |
| 19 | L11 | SCK | IOA/MA/AA = 57.5/35/7.5 | 9.7 |
| 20 | L9 | SCK | 2-EHA/BA/AA = 48/47.5/4.5 | 10.2 |
| 21 | L12 | SCK | 2-EHA/BA/AA = 48/47.5/4.5 | 10.1 |
| 22 | L10 | SCK | IOA/AA + Tackifier = 93/7 | 10.2 |
| 23 | L13 | SCK | IOA/AA + Tackifier = 93/7 | 10.4 |

TABLE 4-continued

Coating weights of adhesive formulations as specified in Table 3.

| Coating Number | Formulation No. | Liner | Adhesive Composition | Coating Weight (grains/ 4" × 6") |
|---|---|---|---|---|
| 24 | L17 | SCK | IOA/AA = 90/10 | 10.1 |
| 25 | L22 | SCK | IOA/AA = 90/10 | 10.0 |
| 26 | L19 | SCK | IOA/AA = 90/10 | 10.2 |
| 27 | L21 | SCK | IOA/AA = 90/10 | 9.8 |
| 28 | L22 | SCK | IOA/AA = 90/10 | 9.8 |
| 29 | L22 | SCK | IOA/AA = 90/10 | 9.9 |
| 30 | L20 | SCK | IOA/AA = 90/10 | 9.8 |
| 31 | L1 | PCK | IOA/AA = 90/10 | 10.1 |
| 32 | L18 | SCK | IOA/AA = 90/10 | 10.3 |
| 33 | L24 | SCK | IOA/AA = 90/10 | 10.0 |
| 34 | L22 | SCK | IOA/AA = 90/10 | 10.1 |
| 35 | L23 | SCK | IOA/AA = 90/10 | 10.1 |
| 36 | L14 | PCK | IOA/AA = 90/10 | 10.0 |
| 37 | L15 | PCK | IOA/AA = 90/10 | 10.4 |
| 38 | L16 | PCK | IOA/AA = 90/10 | 10.3 |
| 39 | L23 | SCK | IOA/AA = 90/10 | 13.8 |
| 40 | L23 | SCK | IOA/AA = 90/10 | 6.1 |
| 41 | L23 | SCK | IOA/AA = 90/10 | 10.2 |
| 42 | L22 | SCK | IOA/AA = 90/10 | 10.0 |
| 43 | L25 | SCK | IOA/AA = 90/10 | 10.2 |

Steam Integrator Device Prototypes and Comparative Prototypes

Steam integrator device prototypes were prepared as described in U.S. Pat. No. 4,448,548 using the adhesives described above. The results of Robustness Testing are provided in Table 5. In addition, several prototype designs were tested for run length performance to ensure that the product continued to meet design performance requirements with the leaker reduction present. The Comparative Prototypes are labeled CE, the Prototypes of this disclosure are labeled E.

TABLE 5

| | | Foil/Film | | Ink |
|---|---|---|---|---|
| Example | Coating Number | Delamination (%) | Leaker (%) | Migration (%) |
| CE-1 | 1 | 40% | 0% | 0% |
| CE-2 | 3 | 11% | 0% | 0% |
| CE-3 | 2 | 46% | 2% | 10% |
| CE-4 | 7 | 83% | 26% | 40% |
| CE-5 | 6 | 83% | 40% | 50% |
| CE-6 | 8 | 77% | 46% | 50% |
| CE-7 | 5 | 80% | 43% | 60% |
| CE-8 | 3 | 43% | 3% | 5% |
| CE-9 | 16 | 27% | 1% | 7% |
| CE-10 | 9 | 29% | 51% | 71% |
| CE-11 | 13 | 54% | 36% | 50% |
| CE-12 | 17 | 31% | 21% | 40% |
| CE-13 | 11 | 30% | 40% | 59% |
| CE-14 | 10 | 16% | 20% | 41% |
| CE-15 | 14 | 56% | 37% | 64% |
| CE-16 | 12 | 37% | 17% | 43% |
| CE-17 | 15 | 69% | 49% | 71% |
| CE-18 | 23 | 49% | 59% | 79% |
| CE-19 | 18 | 26% | 10% | 23% |
| CE-20 | 37 | 67% | 54% | 71% |
| E-1 | 34 | 0% | 0% | 11% |
| E-2 | 29 | 0% | 0% | 11% |
| CE-21 | 24 | 9% | 14% | 40% |
| E-3 | 33 | 5% | 1% | 17% |
| E-4 | 27 | 5% | 2% | 16% |
| E-5 | 35 | 2% | 1% | 10% |
| CE-22 | 38 | 80% | 70% | 82% |
| CE-23 | 32 | 9% | 9% | 17% |
| CE-24 | 36 | 31% | 57% | 70% |
| E-6 | 25 | 6% | 9% | 29% |
| CE-25 | 30 | 0% | 3% | 23% |
| E-7 | 28 | 0% | 0% | 14% |
| CE-26 | 26 | 9% | 6% | 54% |
| CE-27 | 31 | 0% | 34% | 50% |
| E-8 | 41 | 0% | 0% | 30% |
| E-9 | 43 | 0% | 0% | 33% |
| E-10 | 39 | 0% | 0% | 10% |
| E-11 | 40 | 0% | 0% | 20% |
| E-12 | 42 | 0% | 0% | 31% |

ISO Testing

To confirm the suitability of the devices, additional devices were built and fully tested according to ISO 11140-1 (2014): Type 5 Integrating Indicator Requirements and found to pass all requirements.

What is claimed is:

1. A sterilization indicator comprising:
a first substrate with a first major surface and a second major surface, wherein the second major surface comprises a compartment containing a fusible indicator material, and a channel in contact with the compartment for a molten indicator material to flow, and a wicking material in contact with the channel;
a second substrate with a first major surface and a second major surface, wherein the second major surface comprises a transparent segment aligned to overlay the wicking material; and
a high temperature sealing pressure sensitive adhesive layer in contact with at least a portion of the second major surface of the first substrate and the first major surface of the second substrate,
wherein the pressure sensitive adhesive layer comprises a (meth) acrylate-based pressure sensitive adhesive matrix and a high temperature sealing agent, the high temperature sealing agent is essentially unreactive with the (meth) acrylate-based pressure sensitive adhesive matrix at ambient temperature and reacts with the (meth) acrylate-based pressure sensitive adhesive matrix at temperatures of at least 121° C. to form a heat-sealed adhesive bond, and the heat-sealed adhesive bond has increased adhesion compared to the bond of the pressure sensitive adhesive layer without the high temperature sealing agent.

2. The sterilization indicator of claim 1, wherein the (meth) acrylate-based pressure sensitive adhesive matrix comprises at least one (meth) acrylate copolymer comprising at least one alkyl (meth) acrylate comprising 1-12 carbon atoms, and at least one copolymerizable acid-functional monomer.

3. The sterilization indicator of claim 2, wherein the at least one (meth) acrylate copolymer further comprises a crosslinker.

4. The sterilization indicator of claim 2, wherein the at least one alkyl (meth) acrylate comprises 4-12 carbon atoms.

5. The sterilization indicator of claim 1, wherein the high temperature sealing agent comprises a combination of a thermal free radical generator capable of hydrogen abstraction and an acid-reactive compound.

6. The sterilization indicator of claim 5, wherein the thermal free radical generator comprises a peroxide with an activation temperature of at least 100° C.

7. The sterilization indicator of claim 6, wherein the thermal free radical generator comprises an alkyl or aryl peroxide.

8. The sterilization indicator of claim 7, wherein the thermal free radical generator comprises benzoyl peroxide.

9. The sterilization indicator of claim 5, wherein the acid-reactive compound comprises an epoxy-functional compound or a multi-functional compound comprising epoxy-functionality.

10. The sterilization indicator of claim 5, wherein the acid-reactive compound comprises an epoxy-functional silane.

11. The sterilization indicator of claim 10, wherein the epoxy-functional silane comprises (3-glycidyloxypropyl) trimethoxysilane.

12. The sterilization indicator of claim 1, wherein the first substrate comprises a metal foil, and the second substrate comprises a polymeric film.

13. A method of using a sterilization indicator comprising:
providing a sealable sterilization package;
providing medical instruments to be sterilized;
providing a sterilization indicator of claim 1;
sealing the medical instruments and the sterilization indicator in the sterilization package; and
heating the sealed package to sterilize the medical instruments, wherein the indicator comprises;
a first substrate with a first major surface and a second major surface, wherein the second major surface comprises a compartment containing a fusible indicator material, and a channel in contact with the compartment for the molten indicator material to flow, and a wicking material in contact with the channel;
a second substrate with a first major surface and a second major surface, wherein the second major surface comprises a transparent segment aligned to overlay the wicking material; and
a high temperature sealing pressure sensitive adhesive layer in contact with at least a portion of the second major surface of the first substrate and the first major surface of the second substrate,
wherein the pressure sensitive adhesive layer comprises a (meth) acrylate-based pressure sensitive adhesive matrix and a high temperature sealing agent, wherein the high temperature sealing agent is essentially unreactive with the (meth) acrylate-based pressure sensitive adhesive matrix at ambient temperature and reacts with the (meth) acrylate-based pressure sensitive adhesive matrix at temperatures of at least 100° C. to form a heat-sealed adhesive bond, wherein the heat-sealed adhesive bond has increased adhesion compared to the bond of the pressure sensitive adhesive layer without the high temperature sealing agent.

14. The method of claim 13, wherein the sterilization indicator passes the ISO 11140-1 (2014) standard.

* * * * *